United States Patent [19]

Cormier et al.

[11] 4,176,006
[45] Nov. 27, 1979

[54] ENZYME IMMOBILIZATION WITH A DISULPHIDE BRIDGE

[75] Inventors: Richard A. Cormier, St. Hubert; Claude F. Gagnon, Repentigny, both of Canada

[73] Assignee: Redpath Sugars Limited, Montreal, Canada

[21] Appl. No.: 869,239

[22] Filed: Jan. 13, 1978

[51] Int. Cl.$^2$ .................. C12D 13/00; C07G 7/02
[52] U.S. Cl. .................... 435/74; 435/176; 435/174
[58] Field of Search ............. 195/63, 68, DIG. 4, 195/31 F

[56] References Cited

U.S. PATENT DOCUMENTS

| 3,198,781 | 8/1965 | Benesch et al. | 260/117 |
|---|---|---|---|
| 3,519,538 | 7/1970 | Messing et al. | 195/63 |
| 3,846,306 | 11/1974 | Barker et al. | 195/63 X |
| 3,884,761 | 5/1975 | Comling | 195/68 |
| 3,904,478 | 9/1975 | Dean et al. | 195/63 |
| 4,008,126 | 2/1977 | Keyes | 195/63 |
| 4,069,106 | 1/1978 | Stanley et al. | 195/63 X |
| 4,113,565 | 9/1978 | Hurst | 195/31 F |

*Primary Examiner*—David M. Naff
*Attorney, Agent, or Firm*—Browdy and Neimark

[57] ABSTRACT

Immobilized enzymes are provided in which the enzyme is covalently linked by a disulphide group-containing bridge to on inorganic or organic support carrier. Immobilizing by this method enables spent immobilized enzyme to be readily regenerated by reduction under mild conditions of the disulphide bridge to provide the carrier with mercaptan groups, and adding fresh enzyme to the carrier. The immobilization method is applicable to a wide variety of enzymes using the same chemical coupling reagents. The method is especially useful for immobilizing expensive enzymes such as glucose isomerase.

18 Claims, No Drawings

ENZYME IMMOBILIZATION WITH A DISULPHIDE BRIDGE

BACKGROUND OF THE INVENTION (a) Field of the Invention

This invention relates to insolubilized enzymes and their preparation; more especiallly the invention is concerned with a method of preparing an insolubilized, enzymatically active substance, which is applicable to a wide variety of enzymes; the invention further relates to a method of regenerating a carrier material for the enzymes, from spent, insolubilized enzyme.

(b) Description of Prior Art

Enzymes have found wide application in industry in view of their ability to initiate, promote and govern the course of a chemical or biological reaction. The enzyme can be considered as a catalyst since it does not become a part of the product formed in the reaction. On the other hand, the enzyme eventually becomes inactive or spent after taking part as a catalyst in a chemical or biological reaction.

Various techniques have been developed to produce enzymatically active substances in a physical form such that they can be used in industrial processes. The art has in general referred to such techniques as comprising the "immobilization" of the enzyme.

The objective of such immobilization may be, for example, to insolubilize the enzyme relative to a particular solvent, usually water; or to support the enzyme on an inert carrier such that a bed of enzymatically active substance is formed; or, indeed, the immobilization may be to achieve both these objectives and other objectives.

Enzymes have been immobilized on inorganic and organic carrier materials in a number of ways, for example, entrapment in polymeric gels, chemical coupling with organic or inorganic supports, microencapsulation and adsorption on various porous materials, for example glass, cellulose, activated carbon and metal oxides.

Canadian Pat. No. 688,111, Ephraim Katchalski, issued June 9, 1964, describes water-insoluble enzyme substances in which the enzyme is linked to a polymeric water insoluble carrier by a chain formed polymeric link. Canadian Pat. No. 830,477, Avraham Patchornik, issued Dec. 23, 1969, describes the bonding of an enzyme via one of its functional groups to cellulose by reaction with bromoacetyl cellulose. Canadian Pat. No. 945,921, Ralph A. Messing et al, issued Apr. 23, 1974, describes the use of a silane coupling agent to insolubilize an enzyme on an inorganic support, in which the inorganic silicon portion of the coupling agent is attached to the inorganic support and the organic portion of the coupling agent is attached to the enzyme.

The prior coupling methods in the main require the use of a coupling agent for the enzyme and carrier, which contains an appropriate functional group to react with a functional group of the enzyme which is not essential to the enzyme activity, at least in the reaction in which the enzyme is to be employed. These prior coupling methods necessitate the selection of coupling agents with particular functional groups for employment with particular enzymes.

Furthermore, in the prior immobilized enzymes, when the enzyme activity is spent and the enzyme becomes inactive, the spent enzyme and its carrier material are discarded resulting in loss of the carrier material.

SUMMARY OF THE INVENTION

The present invention provides a simple method of immobilizing an enzyme on a carrier material which can be applied to a wide variety of enzymes using the same chemical coupling reagents, thereby avoiding any necessity to select particular coupling reagents with particular functional groups for specific enzymes.

Furthermore the immobilized enzyme substance of the invention has the important advantage that the carrier material can be regenerated from the spent material in which the enzyme has become inactive after use.

According to the invention there is provided a method of making an insolubilized, enzymatically active substance comprising reacting together an enzyme having available mercaptan groups with an insoluble support carrier bearing mercaptan groups such that a disulphide group is produced in a covalent bridge linking said enzyme to said insoluble support carrier; said mercaptan group bearing carrier having the formula

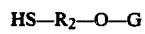

$HS-R_2-O-G$ in which G is the support carrier and $R_2$ is a straight chain or branched, saturated or unsaturated, divalent organic radical.

According to another aspect of the invention there is provided a method of regenerating a mercaptan group bearing support carrier from a spent, insolubilized enzyme substance comprising reducing a disulphide group in a spent insolubilized enzyme substance, in which the enzyme is linked to an insoluble support carrier by a covalent bridge containing the disulphide group, with a reducing agent effective to reduce a disulphide group to mercaptan groups, and recovering the insoluble support carrier bearing mercaptan groups.

According to yet another aspect of the invention there is provided an insolubilized, enzymatically active substance comprising an enzyme linked by a disulphide group-containing covalent bridge to an insoluble support carrier; said bridge comprising a bond structure between said disulfide group and said support carrier of formula

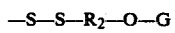

$-S-S-R_2-O-G$ in which G is the support carrier and $R_2$ is a straight chain or branched, saturated or unsaturated, divalent organic radical.

According to a still further aspect of the invention there is provided in industrial chemical or biological processes which employ an enzyme, the improvement wherein the enzyme is in the form of an insolubilized, enzymatically active substance of the invention. One such industrial process is the isomerisation of glucose to fructose employing glucose isomerase (E.C.5.3.1.18) or xylose isomerase (E.C.5.3.1.5).

DESCRIPTION OF PREFERRED EMBODIMENTS (i) Immobilizing Process

In essence, in the process of the invention, the enzyme is chemically coupled to the carrier material through a disulphide bridge which can be readily broken to permit regeneration of the carrier material after the enzyme activity of the immobilized enzyme is spent.

In a first step it is necessary that, both the enzyme and the support carrier be enriched with mercaptan groups. In the particular case where the enzyme is one having a sufficient number of mercaptan groups in its molecular structure, for example, trypsin, enrichment of the enzyme with mercaptan groups may be omitted. In the case of most enzymes, however, enrichment of the enzyme with mercaptan groups is necessary.

(a) Enrichment of support carrier

The support carrier is an inorganic or organic carrier having available nucleophilic functional leaving groups at its surface which are displaceable by hydroxyl groups, suitable leaving groups, include, for example, hydroxyl, hydroxide, oxide and halogen. The support carrier must have the necessary physical properties having regard to the environment in which the immobilized enzyme is to be employed; particularly the support carrier should be insoluble in any solvents which will be employed in the reaction in which the enzyme is to take part. Generally it is necessary that the support carrier be water-insoluble, aqueous systems being the most widely employed in enzyme reactions.

It is necessary too that the support carrier have the requisite physical strength to retain its form in use.

Suitable inorganic support carriers include metal oxides, for example, titanium oxide, nickel oxide, aluminium oxide and hydroxy apatite; lime; siliceous materials, for example, glass, bentonite, wollastonite, colloidal silica and silica gel; and ceramics.

There may also be employed as support carriers substances which have been functionalized by the introduction of a nucleophilic leaving group, for example, hydroxyl, one such example is activated carbon which can be functionalized by the introduction of hydroxyl groups.

Suitable organic carriers include polymers and copolymers which have available hydroxyl groups or other functional groups which are leaving groups displaceable in a nucleophilic substitution reaction.

Inorganic support carriers are especially preferred and particularly suitable are those having a surface area of about 5 to 1600 sq.m/g; among inorganic support carriers, porous glass beads are particularly preferred in view of their good stability towards mechanical attrition, fouling and heat, and their ease of handling; furthermore porous glass beads present a high surface area.

Suitable glass beads may have, by way of example, a specific pore size of 200Å to 1000Å, and a surface area of 5 to 100 sq.m/g. The particular pore size used depends to some extent on the enzyme being immobilized, and it appears that an optimum lower pore size exists for certain enzymes. While the inventors do not wish to be bound by a particular theory it seems probable that the optimum lower pore size will depend on the size of the enzyme molecule. In the case of large enzyme molecules it is probably necessary that the pore size be sufficiently large to accommodate the enzyme molecules without restraining the enzyme molecules in a manner which might affect the enzyme activity.

The enrichment of a glass support carrier with mercaptan groups is easily achieved by reacting the glass with a mercapto alcohol of formula (I)

$$HO-R_2-SH \quad (I)$$

in which $R_2$ is a straight chain or branched, saturated or unsaturated divalent, organic radical which is preferably but not necessarily inert in the enrichment reaction and the subsequent reactions.

Suitable organic radicals include divalent hydrocarbon radicals, including aliphatic radicals and radicals which include both aliphatic and aromatic groups in a chain; included among the aliphatic radicals are saturated aliphatic radicals, for example, alkylene and cyclic radicals and aliphatic radicals having olefinic groups therein.

It is also possible to include a variety of substituents in the organic radical, for example, halogen, alkoxy, for example, methoxy or ethoxy, acyl, for example, acetyl and amino. In the case where the organic radical is a branched radical, the side branches, for example, alkyl or aryl may be considered as substituents in the chain.

It is also possible to include intervening groups in the organic radical, separating aliphatic groups or aliphatic and aromatic groups, for example, ether groups.

It will be understood that substituents and intervening groups should be avoided which might interfere with the enrichment reaction; with the coupling reaction of the enzyme and the support; with the activity of the enzyme in the immobilized enzyme; or with the industrial reaction in which the enzyme is employed.

It will be recognized that the particular nature of $R_2$ is not important provided that it does not interfere in any significant way with the various reactions and the environment of use.

An especially preferred organic radical $R_2$ is an alkylene chain $-(CH_2)_n-$, in which n is an integer from 1 to 20. It seems appropriate to have n as large as possible so as to increase the distance between the hydroxyl group and the mercaptan group. If n is large the enzyme will have more freedom and can thus behave in a manner more closely simulating the free enzyme. From the standpoint of availability and economics, however, n will usually be an integer of from 1 to 6 and more usually 2 to 4. A particularly useful mercapto alcohol having regard to cost and availability is mercaptoethanol (n=2).

It will be understood, however, that if long chain mercapto alcohols became more readily economically available then there use would be preferred for the aforementioned reasons.

In the case where the support carrier comprises glass beads and the mercapto alcohol is of formula $$HO-(CH_2)_n-SH,$$

the hydroxyl group of the alcohol being more nucleophilic than the mercaptan group reacts with the glass to produce a stable ethereal type bond (II)

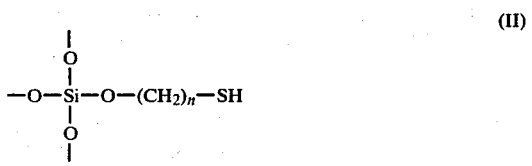

(II)

It is believed that the oxygen of the ethereal-type bond originates in the mercapto alcohol (I) and that the particular reaction with glass beads proceeds as follows:

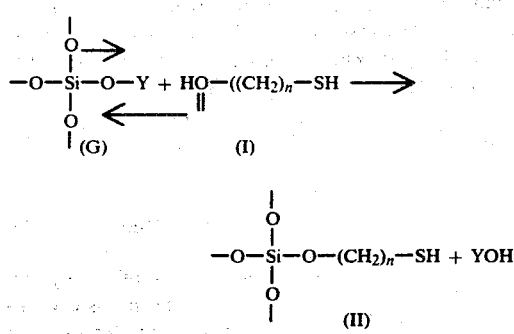

The radical Y is typically hydrogen in which case the reaction proceeds with the elimination of water.

It will be understood, therefore, that G in the formula of the mercaptan bearing carrier is perhaps more correctly considered as the residue of the support carrier, the original radical OY having been displaced, at least in the case where the carrier comprises glass beads. In the case where the carrier is one which has previously been enriched with functional groups, for example, hydroxyl groups, then G is more correctly described as the carrier.

For convenience G is defined simply as the carrier, notwithstanding that 'G' in the mercapto enriched carrier is not necessarily identical with 'G' in the untreated carrier, although in some cases it will be the same. For practical purposes they can be considered as being the same.

Prior to the enrichment of the support carrier with mercaptan groups it is desirably treated to remove any contaminants which may be present.

In the case of a glass support carrier this treatment may suitably comprise immersing the glass in concentrated nitric acid to dissolve any contaminants, washing the glass carrier with distilled water and drying in a muffle furnace at an elevated temperature of 550° C. to 600° C. The glass can then be reacted with the chosen mercapto alcohol to enrich it with mercapto groups.

The enrichment of the support carrier with the mercapto alcohol (I), can suitably be carrier out using the mercapto alcohol itself as the solvent for the enrichment reaction. Usually mercapto alcohols are liquids with high boiling points, usually about 165° C. or higher, such that the enrichment can be achieved under refluxing temperature conditions. The refluxing is suitably contained for 5 to 18 hours to complete the enrichment; the unused mercapto alcohol is easily recovered by distilling it off and can be used in further enrichment processes.

In this way it is possible to obtain glass beads bearing from about 15 to about 80, preferably about 20 to about 80 and more preferably about 35 to about 50 microequivalents of mercapto groups per gram of beads.

(b) Enrichment of enzyme

In the case where the enzyme does not contain sufficient available mercapto groups in its molecular structure it must be enriched in mercapto groups. Suitably this enrichment makes use of amino groups present in all enzymes.

This enrichment comprises reacting the amino groups in the enzyme to produce a classical peptide linkage with a mercaptan-group containing reagent; a mixed anhydride coupling procedure conducted in a solvent, for example water, is especially useful.

The enrichment results in a mercapto group bearing enzyme which can be represented by the formula (III)

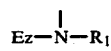

in which

is the residue of an enzyme having lost a hydrogen atom from the amino group; and R is a straight chain or branched, saturated or unsaturated, divalent organic radical which may suitably be selected from the same radicals as $R_2$.

The nature of $R_1$ will depend on the particular enzyme. When the amino group in the enzyme is a primary amino group, $R_1$ will be hydrogen; however, when the amino group in the enzyme is a secondary amino group, then $R_1$ will correspond to the subsituent in the secondary amino group in the enzyme. $R_1$ may be, for example, a lower alkyl group or it may be a long chain alkylene group the remote end of which is connected to a different part of the enzyme.

The preferred substituent R is the same as the preferred substituent $R_2$, namely, an alkylene radical of formula $(CH_2)_n$ where n is an integer from 1 to 20, usually 1 to 6, and more usually 2 to 4. However, R and $R_2$ may be the same or different.

The mixed anhydride employed to enrich the enzyme is suitably one of formula (IV)

in which $R_3$ is preferably a lower alkyl group of 1 to 6, more preferably 1 to 4 carbon atoms and R is as defined above.

The mixed anhydride (IV) is suitably prepared as needed, immediately prior to the enrichment reaction. It may by synthesized by the reaction of a mercapto carboxylic acid, for example, mercapto propionic acid, with an alkylhalogeno formate, for example, ethylchloroformate, in the presence of an organic base, for example, triethylamine or pyridine.

It is not necessary to isolate the mixed anhydride (IV) from the reaction mixture, and the enzyme can be added directly to the reaction mixture, while the mixture is maintained basic but close to neutral pH 7. The mixture is stirred for 0.1 to 5, preferably 1 to 3 hours at room temperature and the enriched enzyme is precipitated out of the mixture. The precipitation may be achieved by the controlled addition of water miscible organic solvent, for example, an alcohol, typically ethanol or propanol, or by the controlled addition of a highly water soluble salt, for example, ammonium sulphate.

It will be recognized that a wide variety of cell-free enzymes can be enriched with mercaptan groups in this manner, since the enrichment makes use of the amino groups present in enzymes. By way of example there may be mentioned amylase (α-amylase, E.C.3.2.1.1; and β-amylase, E.C.3.2.1.2), glucoamylase (E.C.3.2.1.3), cellulase (E.C.3.2.1.4), maltase (E.C.3.2.1.20), invertase (E.C.3.2.1.26), lastase or β-galaosidase (E.C.3.2.1.23), glucose isomerase (E.C.5.3.1.18), xylose isomerase (E.C.5.3.1.5).

(c) Coupling reaction

Reaction between the enzyme bearing mercaptan groups and the support carrier having mercaptan groups to produce a disulphide group linking the enzyme and the support carrier can be carried out under simple reaction conditions.

The reaction between two mercaptan groups to form a disulphide linkage can be considered as being an oxidation reaction, and is suitably conducted in the presence of a catalyst which can be considered an oxidation catalyst.

Suitable oxidation catalysts include cupric chloride, potassium ferricyanide and an air/alkaline system. An especially preferred oxidation catalyst is sodium selenate, in the presence of trace amounts of oxygen as co-catalyst, the sodium selenate is suitably employed in an amount of 0.005 to about 0.1, preferably about 0.01 mole per mole of mercaptan groups involved. The reaction is carried out at a pH of about 7 to 10, preferably 7.0 to 8.5 near neutrality and a low temperature, preferably, of about 0° C. to about 15° C. Suitably the reaction mixture is allowed to stand for about 1 to 18 hours to complete the coupling reaction.

After completion of the coupling reaction, the immobilized enzyme is washed repeatedly with buffered sodium chloride solutions to remove any adsorbed enzyme; and the insolubilized enzyme is ready for use.

If necessary the insolubilized enzyme can be stored prior to use; in this case it is desirably stored in a buffered solution at a pH at which the insolubilized enzyme is found to have its highest enzyme activity. The insolubilized enzyme is suitably stored at a temperature of about 0° C. to about 10° C.; in this way it is found that the enzyme activity can be maintained constant for several weeks to several months.

Thus employing a modified enzyme of formula (III) and a support carrier functionalized with a mercapto alcohol of formula (I), there is obtained an insolubilized enzymatically active substance of formula (V)

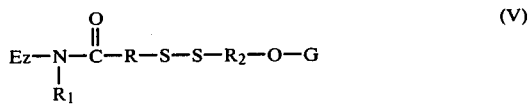

in which

R, R$_2$ and G are as defined above.

It will be understood that there may be more than one disulphide group linkage between each enzyme molecule and the support material.

Consequently the structural formula, such as (II), (III) and (V), represent the simplest possible situation in which each enzyme molecule is linked by a single disulphide group containing bridge to a hypothetical single molecule of the support carrier. It will be understood that these structural formulae are not to be construed, either in the disclosure or the claims, as restricting the scope of the invention to embodiments in which there is a single disulphide group-containing bridge between each enzyme molecule and each real or hypothetical support carrier molecule.

(ii) Enzyme Catalyzed Reactions

As described previously the immobilized enzymes are employed in a variety of industrial processes. Such processes may be conducted in a variety of reactors, for example, in a batch reactor; in a continuously stirred tank; in a fluidized bed; in a packed bed column; or in a moving packed bed column.

Of particular interest is the use of immobilized enzymes in the isomerization of glucose to levulose to produce a syrup containing glucose and levulose for use in place of sucrose as a sweetening additive.

Different enzymes have been employed to isomerize glucose to levulose, notably glucose isomerase (E.C.5.3.1.18) sometimes referred to as dextrose isomerase; and xylose isomerase (E.C.5.3.1.5); these enzymes are sometimes generally referred to as isomerase.

These enzymes all have the ability to isomerize glucose to levulose although they may also have other activities. The isomerases may be obtained from a variety of microbial sources, and the properties of isomerases derived from different sources may differ slightly.

The glucose containing syrups which are isomerized to levulose-containing syrups are suitably prepared by the hydrolysis of starch; and commercially cornstarch is usually employed. Thus the starch hydrolysate serves as the substrate on which the enzyme acts.

The starch hydrolysate is suitably made by an acid or enzymatic hydrolysis, or a combination thereof. In one operation the starch hydrolysate is produced by acid or enzyme hydrolysis to a D.E. (dextrose equivalent) of 10 or less, followed by enzymatic saccharification to a D.E. which is preferably above 95.

An immobilized enzyme of this invention in which one of the isomerases which isomerize glucose to levulose is insolubilized on glass beads is especially useful when employed as a packed bed in a vertical column for the isomerization of glucose to levulose, the glucose syrup passing continuously through the packed bed, preferably in a downward direction, and possibly through a series of packed columns.

In conventional packed beds of immobilized enzymes of this kind it is necessary to remove the packed bed from the column when the enzyme is spent or becomes inactive, and then refill the column with fresh immobilized enzyme; this emptying and refilling of the column is both time consuming and costly.

In the present invention it is possible to regenerate support carrier bearing the mercaptan groups in situ in the packed column, with removal of the inactive enzyme; and to immobilize fresh active enzyme on the support carrier in the packed column; this becomes possible in view of the moderate process conditions required for regeneration of the support carrier bearing mercaptan groups; and the moderate conditions required for the coupling reaction to form the disulphide group-containing bridge.

Thus in addition to avoiding waste of the support carrier by providing a simple method for regenerating the carrier material the present invention permits the regeneration and subsequent coupling reaction to insolubilize fresh active enzyme to be carried out in situ in the reaction vessel in which the immobilized enzyme is employed.

(iii) Regeneration of Support Carrier

The carrier material comprising the insoluble support carrier bearing mercaptan groups can be readily regenerated from the spent, insolubilized enzyme substance in which the enzyme has become inactive after prolonged use.

This regeneration essentially comprises splitting or reducing the disulphide group to form the original mercaptan groups. The splitting of the disulphide group is achieved with a reducing agent, which is conveniently in a liquid phase so that it can run through a bed of the spent, insolubilized enzyme substance. A suitable reducing agent is a thioalcohol which is conveniently the same one, of formula (I), as was used in the enrichment of the support carrier. The regeneration is suitably carried out with the pure thioalcohol, which also acts as the solvent, at a temperature of 60° C. to the boiling point of the thioalcohol.

The carrier material is then washed with distilled water and is ready for an immobilization coupling reaction.

The invention is further illustrated by the following examples, which are not intended to be construed as limiting the scope of the invention.

EXAMPLE 1

(a) Preparation of the carrier

Siliceous porous glass beads having a specific pore size of 500Å (available from Bio-Rad Laboratories under catalogue number 152-0440) were washed in concentrated nitric acid at 60° C. for 2 hours. The beads were then washed with deionized water until the pH was close to neutral; finally the glass beads were dried by heating in a muffle furnace at 550° C. for 18 hours.

After cooling, the glass beads (10 g) were placed in a boiling flask and 25 ml of 2-mercaptoethanol was added. The mixture was allowed to reflux (165°–175° C.) for 5 hours.

The resulting enriched material was filtered, residual 2-mercaptoethanol being recuperated, and washed with deionized water until no more thiol groups were detected in the filtrate.

The mercaptan functionalized glass beads were titrated to determine their thiol group content by means of a back-titration method using p-hydroxymercuribenzoate, and were found to have 70μ eq. of —SH groups per gram.

The mercaptan functionalized glass beads were stored for further usage in a cool dry place after drying under a vacuum.

(b) Preparation of the Enzyme

Bacterial α-amylase (E.C.3.2.1.1), found to have no free thiol groups, was enriched with thiol groups prior to coupling with the carrier described in Example 1(a).

A mixed anhydride was prepared by dissolving 200 mg of n-mercapto propionic acid in 5 ml of deionized water and then brought to a neutral pH by addition of a 3% NaOH solution. To the mixture, 20 mg of triethylamine followed by 200 mg of ethyl chloroformate were added and the mixture was then stirred until the pH became constant at about 6.3.

To the mixture was added 100 mg of crystalline bacterial α-amylase dissolved in 1 ml of a phosphate buffer (pH 6.9) and the resulting mixture was stirred for 3 hours, while maintaining the pH contant at about 7.5.

The resulting modified enzyme was precipitated from solution by means of careful additions of ethanol. The precipitate was centrifuged, decanted and submitted to several washings with ethanol. The modified enzyme was then dissolved in a phosphate buffer (pH 6.9). It was found to be enriched to an extent of 5 to 10 μM of thiol groups per gram using the same back titration method as described in Example 1(a).

(c) Coupling procedure

The treated glass beads, obtained in Example 1(a) (1 g; 500Å pore size) were contacted with a solution of 100 mg of the modified α-amylase obtained in Example 1(b)in 4 ml of a phosphate buffer (pH 7.5) and 1 ml of a 2% starch solution and 50 μl of $Na_2SeO_3$ (0.01 M); and the mixture was maintained for 18 hours at 5° C.

The resulting immobilized enzyme was washed several times to remove excess enzyme. The washings were carried out sequentially with a phosphate buffer (pH 6.9) and a 0.5 M NaCl solution in the same phosphate buffer. Finally the material was washed for 2 hours at 70° C. with a NaCl (0.1 M)—$CaCl_2$ (0.01 M) solution.

The enzyme activity, as measured by Bernfeld's DNSA method, was between 200 and 400 units/g of material and 4 to 10 mg of protein were found to be present per gram of glass.

The immobilized enzyme was stored at a temperature of 5° C. The stability of the immobilized α-amylase enzyme is demonstrated by the results of tests of the activity set out in the table below.

| No. of days since immobilization | Activity (Units/g) |
| --- | --- |
| 0 | 224 |
| 57 | 221 |
| 76 | 228 |
| 118 | 240 |

The above tabulated results demonstrate that within the confines of the procedure employed to determine the activity, the activity of the immobilized enzyme remained substantially unchanged.

(d) Regeneration process 2 grams of α-amylase, immobilized as in Example 1(c) and with a very low activity resulting from a prolonged utilization, were treated in situ in a jacketted column through which 50 ml of mercaptoethanol were continuously recirculated at 95° C. for 18 hours.

The thus treated glass beads are sequentially washed with deionized water and a solution of sodium chloride (0.05 M) in a phosphate buffer (pH 6.9). The glass beads were then ready to be submitted to a subsequent re-coupling procedure as illustrated below. If required it was found that they could be stored at 5° C. once dried under vacuo.

(e) Reuse of the Regenerated Carrier

As indicated in Example 1(d), the regenerated support can be used immediately in a coupling procedure. In this way, the same glass beads can be used repeatedly. In other words each time the enzyme immobilized on the beads is inactivated, the beads can be regenerated and fresh active-enzyme immobilized thereon. This results in a prolonged ultization of the carrier material and thus effects a considerable economy.

This is illustrated with immobilized α-amylase in the table below.

| No. of immobilization | Activity after immobilization (Units/g) |
| --- | --- |
| 1 | 220 |
| 2 | 166 |
| 3 | 190 |

This demonstrates that the ability of the glass beads to immobilize the enzyme is not affected by repeated regeneration of the beads.

EXAMPLE 2

Immobilization of Glucose Isomerase on Glass Beads

Glucose isomerase (E.C.5.3.1.18), from Actinoplanes cells, was enriched in thiol groups by the mixed anhydride method described in Example 1(b).

The thus enriched enzyme was subjected to the coupling procedure described in Example 1(c) as follows.

100 mg of the enriched glucose isomerase were dissolved in a 10 ml aqueous solution comprising—0.01 M $MgSO_4 \cdot 7H_2O$ and 0.0004 M $CoSO_4 \cdot 7H_2O$ at a pH of 8.

1 g of glass beads treated in accordance with Example 1(a) and 50 μl of a 0.01 $Mna_2SeO_3$ solution were added. The mixture was allowed to stand at 5° C. for 18 hours.

The solid material (immobilized enzyme) was washed sequentially with a 0.5 M NaCl solution and with the solution of $Mg^{++}$—$Co^{++}$ described above (pH 8).

The washed material, liberated of free non-immobilized enzyme displayed an activity of 75 to 100 GIU/g of material (1 GIU being the quantity of "enzyme activity" required to isomerize 1 μmole of glucose to fructose per minute per gram of material). The above figure of activity being measured by means of the Dische and Devi's cysteine, sulphuric acid method, using a batch process and a 40% W/V glucose solution at pH 8 and a temperature of 65° C.

The immobilized glucose isomerase was successfully employed in the isomerization of glucose to levulose. When the activity deteriorated to a low level the carrier was regenerated in accordance with the procedure of Example 1(d) and fresh mercapto enriched glucose isomerase was immobilized on the regenerated carrier.

We claim:

1. An insolubilized, enzymatically active substance comprising an enzyme linked by a disulphide group containing covalent bridge to a support carrier, and having the formula (V)

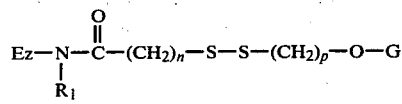

(V)

in which

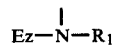

is the residue of an enzyme having lost a hydrogen atom from an amino group, n and p, which may be the same or different, are integers of 1 to 6; and G represents a support carrier comprising glass beads having a specific pore size of 200Å to 1000Å and a surface area of 5 to 10 sq. m/g.

2. An insolubilized substance according to claim 1, wherein

is the residue of an enzyme effective to isomerize glucose to levulose, selected from the group consisting of glucose isomerase and xylose isomerase.

3. A method of making an insolubilized, enzymatically active substance comprising reacting an enzyme having available mercaptan groups, at a temperature of 0° C. to about 15° C., and a pH of 7 to 10 in the presence of an oxidation catalyst, with a support carrier comprising porous glass beads functionalized with mercaptan groups, said beads having a specific pore size of 200Å to 1000Å and a surface area of 5 to 100 sq.m/g., such that a disulphide group is produced in a covalent bridge linking said enzyme to said carrier; said glass beads having been functionalized with mercaptan groups by reaction at the hydroxyl group of a mercapto alcohol of formula (I)

$$HO—(CH_2)_n—SH$$

in which n is an integer of 1 to 6, such that the beads bear mercaptan group-containing radicals of formula $$HS—(CH_2)_n—O—$$

wherein n is as defined above.

4. A method according to claim 3, wherein said oxidation catalyst comprises sodium selenate in the presence of trace amounts of oxygen as co-catalyst, said sodium selenate being present in an amount of 0.005 to about 0.1 moles per mole of mercaptan group; and said pH is 7.0 to 8.5.

5. A method according to claim 3, in which said enzyme is pre-functionalized by introducing mercapto groups therein.

6. A method according to claim 5, in which said enzyme is one into which mercaptan groups have been introduced by reacting the enzyme with a mixed anhydride of formula (IV)

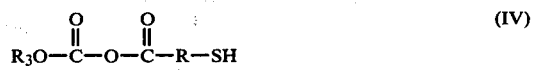

(IV)

in which $R_3$ is a lower alkyl group of 1 to 6 carbon atoms, and R is an alkylene radical of formula —$(CH_2)_n$—, in which n is an integer of 1 to 6, to form an enriched enzyme of formula (III)

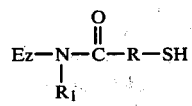

(III)

in which

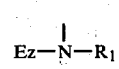

is the residue of an enzyme having lost a hydrogen atom from an amino group, and R is as defined in (IV).

7. A method of making an insolubilized, enzymatically active substance comprising reacting an enzyme pre-functionalized by introducing mercapto groups therein, at a temperature of 0° C. to about 15° C., and a pH of 7 to 8.5 in the presence of a catalytic amount of sodium selenate, with a support carrier comprising porous glass beads functionalized with mercaptan groups, such beads having a specific pore size of 200Å to 1000Å and a surface area of 5 to 100 sq. m/g., such that a disulphide group is produced in a covalent bridge linking said enzyme to said carrier; said glass beads having been functionalized with mercaptan groups by reaction at the hydroxyl group of a mercapto alcohol of formula (I)

HO—(CH$_2$)$_n$—SH in which n is an integer of 1 to 6, such that the beads bear mercaptan group-containing radicals of formula HS—(CH$_2$)$_n$—O— wherein n is as defined above.

8. A method according to claim 7, wherein said sodium selenate is present in an amount of 0.005 to about 0.1 moles per mole of mercaptan groups, and said reacting is carried out in the presence of trace amounts of oxygen as co-catalyst for said sodium selenate.

9. A method according to claim 8, in which said enzyme is one into which mercaptan groups have been introduced by reacting the enzyme with a mixed anhydride of formula (IV)

$$R_3O-\overset{O}{\underset{\|}{C}}-O-\overset{O}{\underset{\|}{C}}-R-SH \quad (IV)$$

in which R$_3$ is a lower alkyl group of 1 to 6 carbon atoms, and R is an alkylene radical of formula —(CH$_2$)$_n$—, in which n is an integer of 1 to 6, to form an enriched enzyme of formula (III)

$$Ez-\underset{\underset{R_1}{|}}{N}-\overset{O}{\underset{\|}{C}}-R-SH \quad (III)$$

in which $$Ez-\underset{\underset{R_1}{|}}{N}$$

is the residue of an enzyme having lost a hydrogen atom from an amino group, and R is as defined in (IV).

10. A method according to claim 7, wherein said enzyme is one effective to isomerize glucose to levulose selected from the group consisting of glucose isomerase and xylose isomerase.

11. A method of making an insolubilized, enzymatically active substance comprising functionalizing an enzyme with mercapto groups by reacting amino groups of the enzyme with a mercaptan group containing reagent with formation of a peptide linkage to produce a mercapto functionalized enzyme, reacting the mercaptan groups of the functionalized enzyme, at a temperature of 0° C. to about 15° C., and a pH of 7 to 8.5 in the presence of an oxidation catalyst, with the mercaptan groups of a support carrier comprising porous glass beads bearing about 35 to about 50 micro-equivalents of mercaptan groups per gram of beads, said beads having a specific pore size of 200Å to 1000Å and a surface area of 5 to 100 sq. m/g. to produce a disulphide group in a covalent bridge linking the enzyme and carrier;

said beads having been functionalized with said mercaptan groups by heating the beads in a mercapto alcohol of formula (I)

HO—(CH$_2$)$_n$—SH in which n is an integer of 2 to 4, under reflux conditions for 5 to 18 hours, to react with the mercapto alcohol at the hydroxyl group thereof, such that the beads bear mercaptan group-containing radicals of formula HS—(CH$_2$)$_n$—O— wherein n is as defined above.

12. A method according to claim 11, wherein said mercapto alcohol of formula (I) is mercapto ethanol.

13. A method of regenerating a mercaptan group bearing support carrier from a spent insolubilized enzyme substance of formula $$Ez^1-\underset{\underset{R_1}{|}}{N}-\overset{O}{\underset{\|}{C}}-(CH_2)_n-S-S-(CH_2)_p-O-G$$

wherein $$Ez^1-\underset{\underset{R_1}{|}}{N}$$

is the residue of a spent enzyme having lost a hydrogen atom from an amino group n and p, which may be the same or different, are integers of 1 to 6 and G represents an inorganic support carrier comprising porous glass beads having a specific pore size of 200Å to 1000Å, prepared by reacting an enzyme having available mercaptan groups, at a temperature of 0° C. to about 15° C., and a pH of 7 to 10 in the presence of an oxidation catalyst with the support carrier after it has been prefunctionalized with mercaptan groups by reacting at the hydroxyl group of a mercapto alcohol of the formula HO—(CH$_2$)$_n$—SH wherein n is as defined above, said enzyme being prefunctionalized with the mercapto groups by reacting the enzyme with a mixed anhydride of formula (IV)

$$R_3O-\overset{O}{\underset{\|}{C}}-O-\overset{O}{\underset{\|}{C}}-R-SH$$

in which R$_3$ is a lower alkyl group of 1 to 6 carbon atoms and R is an alkylene radical of formula —(CH$_2$-

)$_n$—, in which n is an integer of 1 to 6, to form an enriched enzyme of formula (III)

$$Ez-\underset{\underset{R_2}{|}}{N}-\underset{\underset{}{\overset{\overset{O}{\|}}{C}}}-(CH_2)_n-SH$$

in which $$Ez-\underset{\underset{}{|}}{N}-R_1$$

is the residue of an enzyme having lost a hydrogen atom from an amino group, and n is an integer of 1 to 6,
reducing the disulphide group in the spent insolubilized enzyme substance with a thioalcohol of formula (I)

$$HO-(CH_2)_n-SH$$

in which n is an integer of 1 to 6, and recovering the insoluble support carrier bearing mercaptan groups.

14. A method according to claim 13, wherein said enzyme is one effective to isomerize glucose to levulose selected from the group consisting of glucose isomerse and xylose isomerase.

15. A method according to claim 13, wherein said beads have a surface area of 5 to 100 sq. m/g.

16. An improved method for the isomerization of glucose to levulose comprising
(i) reacting together
(a) a modified enzyme having available mercaptan groups of formula (III)

$$Ez-\underset{\underset{R_1}{|}}{N}-\overset{\overset{O}{\|}}{C}-R-SH \qquad (III)$$

in which $$Ez-\underset{\underset{R_1}{|}}{N}$$

is the residue of glucose isomerase or xylose isomerase having a lost a hydrogen atom from an amino group and R is an alkylene radical of formula —(CH$_2$)$_n$—, in which n is an integer of 1 to 6, and
(b) a water insoluble support carrier bearing mercaptan groups of formula $$G-O-R_2-SH$$

in which G represents porous glass beads having a specific pore size of 200Å to 1000Å; and R$_2$ is an alkylene radical of formula —(CH$_2$)$_n$—, in which n is an integer of 1 to 6, to form a water insolubilized, enzymatically active substance of formula (V)

$$Ez-\underset{\underset{R_1}{|}}{N}-\overset{\overset{O}{\|}}{C}-R-S-S-R_2-O-G \qquad (V)$$

in which $$Ez-\underset{\underset{R_1}{|}}{N}-,$$

R, R$_2$ and G are as defined above;
(ii) isomerizing a glucose-containing solution with said enzymatically active substance to produce a levulose containing isomerizate until said enzyme becomes inactive;
(iii) reducing the disulphide group in the spent insolubilized subtance formed in step (ii) to regenerate the insoluble support carrier bearing mercaptan groups of step 1(b);
(iv) reacting the regenerated carrier of step (iii) with fresh, active, modified enzyme of formula (III), as defined above to produce a fresh supply of the water insolubilized, enzymatically active substance (V), as defined above; and
(v) repeating step (ii).

17. A method according to claim 16, wherein said enzymatically active substance in (ii) is packed as a bed in a vertical column and said glucose-containing solution is passed through said bed in (ii), and wherein steps (iii) and (iv) are carried out in said column without removal of the bed therefrom.

18. A method according to claim 16, wherein said beads have a surface area of 5 to 100 sq. m/g.

* * * * *

UNITED STATES PATENT AND TRADEMARK OFFICE
CERTIFICATE OF CORRECTION

PATENT NO. : 4,176,006
DATED : November 27, 1979
INVENTOR(S) : CORMIER et al

It is certified that error appears in the above-identified patent and that said Letters Patent are hereby corrected as shown below:

Column 11, line 65, "5 to 10" should read --5 to 100--

Signed and Sealed this

Fourth Day of November 1980

[SEAL]

Attest:

SIDNEY A. DIAMOND

Attesting Officer

Commissioner of Patents and Trademarks